US010039642B2

(12) United States Patent
Hillukka

(10) Patent No.: US 10,039,642 B2
(45) Date of Patent: Aug. 7, 2018

(54) SYSTEM FOR LOADING A COLLAPSIBLE HEART VALVE

(71) Applicant: St. Jude Medical, Cardiology Division, Inc., St. Paul, MN (US)

(72) Inventor: Brett Allen Hillukka, Hanover, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 15/475,845

(22) Filed: Mar. 31, 2017

(65) Prior Publication Data

US 2017/0202667 A1   Jul. 20, 2017

Related U.S. Application Data

(60) Division of application No. 14/534,893, filed on Nov. 6, 2014, now Pat. No. 9,642,703, which is a
(Continued)

(51) Int. Cl.
*A61F 2/24* (2006.01)
*A61F 2/95* (2013.01)

(52) U.S. Cl.
CPC .......... *A61F 2/2436* (2013.01); *A61F 2/2418* (2013.01); *A61F 2002/9522* (2013.01); *A61F 2250/0039* (2013.01)

(58) Field of Classification Search
CPC ................. A61F 2/2436; A61F 2/2418; A61F 2250/0039; A61F 2002/9522
See application file for complete search history.

(56) References Cited

U.S. PATENT DOCUMENTS 3,657,744 A   4/1972   Ersek
4,423,730 A   1/1984   Gabbay
(Continued)

FOREIGN PATENT DOCUMENTS

EP   1129744 A1   9/2001
EP   1157673 A2   11/2001
(Continued)

OTHER PUBLICATIONS

Ruiz, Carlos, Overview of PRE-CE Mark Transcatheter Aortic Valve Technologies, Euro PCR, dated May 25, 2010.
(Continued)

*Primary Examiner* — John C Hong
(74) *Attorney, Agent, or Firm* — Lerner, David, Littenberg, Krumholz & Mentlik, LLP

(57) ABSTRACT

An assembly for collapsing a self-expanding prosthetic heart valve includes a compression member, a support member and a constricting member. The compression member has a tapered wall between its first open end and its second open end, the tapered wall defining an open space adapted to receive the valve. The support member has a base and a recess adapted to receive an end of the valve. The support member and the compression member are movable toward one another to compress the valve and push it through a relatively small aperture in the second open end of the compression member. The second end of the constricting member is sized to receive the compressed valve from the second open end of the compression member for loading into a delivery device.

8 Claims, 13 Drawing Sheets

Related U.S. Application Data continuation of application No. 13/558,942, filed on Jul. 26, 2012, now Pat. No. 8,931,159.

(60) Provisional application No. 61/666,187, filed on Jun. 29, 2012, provisional application No. 61/512,637, filed on Jul. 28, 2011.

(56) References Cited

U.S. PATENT DOCUMENTS

| | | | |
|---|---|---|---|
| 5,843,167 A | 12/1998 | Dwyer et al. |
| 5,924,424 A | 7/1999 | Stevens et al. |
| 5,968,068 A | 10/1999 | Dehdashtian et al. |
| 6,077,297 A | 6/2000 | Robinson et al. |
| 6,132,458 A | 10/2000 | Staehle et al. |
| 6,306,141 B1 | 10/2001 | Jervis |
| 6,471,718 B1 | 10/2002 | Staehle et al. |
| 6,623,518 B2 | 9/2003 | Thompson et al. |
| 6,814,746 B2 | 11/2004 | Thompson et al. |
| 6,830,584 B1 | 12/2004 | Seguin |
| 6,935,389 B1 | 8/2005 | Rinaldi |
| 7,014,074 B1 | 3/2006 | Rinaldi |
| 7,018,406 B2 | 3/2006 | Seguin et al. |
| 7,096,554 B2 | 8/2006 | Austin et al. |
| 7,311,730 B2 | 12/2007 | Gabbay |
| 7,510,572 B2 | 3/2009 | Gabbay |
| 7,682,390 B2 | 3/2010 | Seguin |
| 7,803,185 B2 | 9/2010 | Gabbay |
| 8,561,967 B2 | 10/2013 | Hendriksen et al. |
| 8,562,663 B2 | 10/2013 | Mearns et al. |
| 8,585,019 B2 | 11/2013 | Melsheimer et al. |
| 8,931,159 B2 | 1/2015 | Hillukka |
| 8,973,234 B2 | 3/2015 | Johnson et al. |
| 9,192,469 B2 | 11/2015 | Mearns et al. |
| 9,414,914 B2 | 8/2016 | Duffy et al. |
| 9,414,917 B2 | 8/2016 | Young et al. |
| 9,492,274 B2 | 11/2016 | Johnson et al. |
| 9,675,456 B2 | 6/2017 | Quill et al. |
| 2003/0050694 A1 | 3/2003 | Yang et al. |
| 2003/0070682 A1 | 4/2003 | Wilson et al. |
| 2004/0210304 A1 | 10/2004 | Seguin et al. |
| 2005/0137695 A1 | 6/2005 | Salahieh et al. |
| 2005/0137697 A1 | 6/2005 | Salahieh et al. |
| 2005/0194578 A1 | 9/2005 | Morris |
| 2006/0074484 A1 | 4/2006 | Huber |
| 2006/0106415 A1 | 5/2006 | Gabbay |
| 2006/0135973 A1 | 6/2006 | Hawkins et al. |
| 2006/0142848 A1 | 6/2006 | Gabbay |
| 2006/0167468 A1 | 7/2006 | Gabbay |
| 2006/0259120 A1 | 11/2006 | Vongphakdy et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0073391 A1 | 3/2007 | Bourang et al. |
| 2007/0088431 A1 | 4/2007 | Bourang et al. |
| 2007/0112422 A1 | 5/2007 | Dehdashtian |
| 2007/0162100 A1 | 7/2007 | Gabbay |
| 2007/0168013 A1 | 7/2007 | Douglas |
| 2007/0203575 A1 | 8/2007 | Forster et al. |
| 2007/0239271 A1 | 10/2007 | Nguyen |
| 2007/0244552 A1 | 10/2007 | Salahieh et al. |
| 2007/0270931 A1 | 11/2007 | Leanna et al. |
| 2007/0270932 A1 | 11/2007 | Headley et al. |
| 2008/0071369 A1 | 3/2008 | Tuval et al. |
| 2008/0147182 A1 | 6/2008 | Righini et al. |
| 2008/0221703 A1 | 9/2008 | Que et al. |
| 2009/0054975 A1 | 2/2009 | del Nido et al. |
| 2009/0093876 A1 | 4/2009 | Nitzan et al. |
| 2009/0143857 A1 | 6/2009 | Melsheimer et al. |
| 2010/0004740 A1 | 1/2010 | Seguin et al. |
| 2010/0051886 A1 | 3/2010 | Cooke et al. |
| 2010/0286768 A1 | 11/2010 | Alkhatib |
| 2010/0298931 A1 | 11/2010 | Quadri et al. |
| 2011/0224678 A1 | 9/2011 | Gabbay |
| 2012/0078352 A1 | 3/2012 | Wang et al. |
| 2012/0083875 A1 | 4/2012 | Johnson et al. |
| 2012/0330408 A1 | 12/2012 | Hillukka et al. |
| 2014/0331475 A1 | 11/2014 | Duffy et al. |
| 2015/0101171 A1 | 4/2015 | Johnson et al. |
| 2016/0278955 A1 | 9/2016 | Liu et al. |
| 2017/0035570 A1 | 2/2017 | Johnson et al. |

FOREIGN PATENT DOCUMENTS

| | | |
|---|---|---|
| JP | 2000093523 A | 4/2000 |
| JP | 2009-533139 | 9/2009 |
| WO | 07071436 A2 | 6/2007 |
| WO | 2007081940 A2 | 7/2007 |
| WO | 2007120543 A1 | 10/2007 |
| WO | 08070797 A2 | 6/2008 |
| WO | 2009091509 A1 | 7/2009 |
| WO | 2010014834 A1 | 2/2010 |
| WO | 10051025 A1 | 5/2010 |
| WO | 10087975 A1 | 8/2010 |
| WO | 2010096176 A1 | 8/2010 |
| WO | 2012023979 A2 | 2/2012 |
| WO | 2012036742 A2 | 3/2012 |
| WO | 2012036744 A2 | 3/2012 |
| WO | 2012057983 A1 | 5/2012 |
| WO | 2012106491 A1 | 8/2012 |

OTHER PUBLICATIONS

International Search Report and Written Opinion for Application No. PCT/US2012/023576 dated Jul. 6, 2012.

International Search Report for Application No. PCT/US2012/048307 dated Feb. 28, 2013.

International Search Report for Application No. PCT/US2012/048298 dated Nov. 7, 2012.

Quaden et al., "Percutaneous aortic valve replacement: resection before implantation", pp. 836-840, European J. of Cardio-thoracic Surgery, 27 (2005).

International Search Report for Application No. PCT/US2011/001598 dated Jul. 6, 2012.

FIG. 7
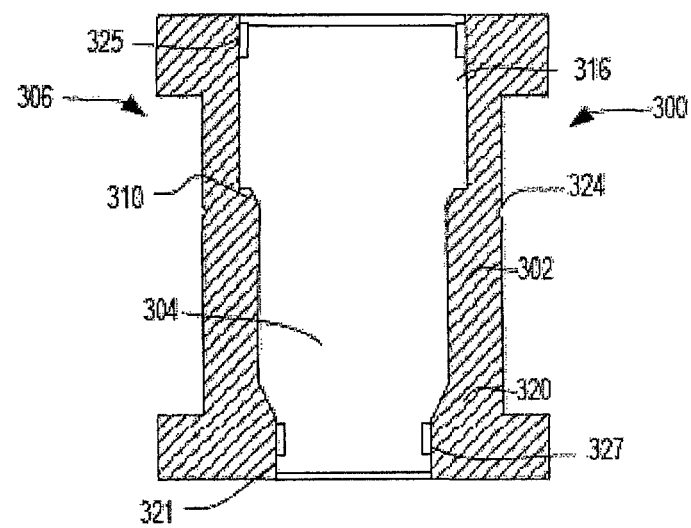
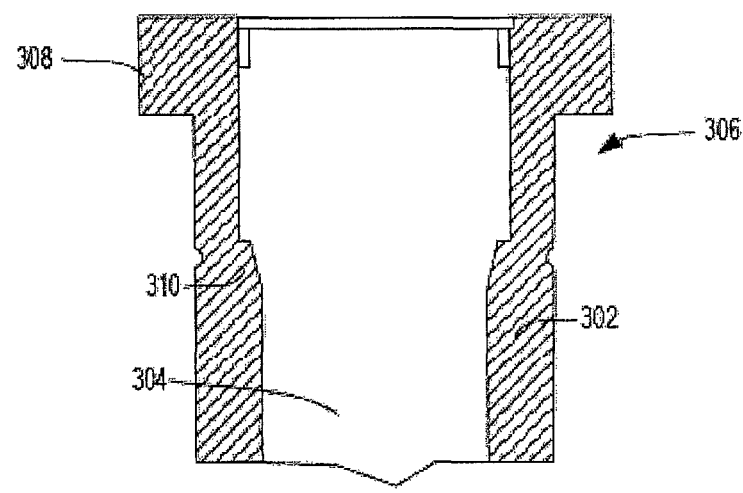
FIG. 8

SYSTEM FOR LOADING A COLLAPSIBLE HEART VALVE

CROSS-REFERENCE TO RELATED APPLICATIONS

This application is a divisional of U.S. patent application Ser. No. 14/534,893, filed Nov. 6, 2014, which is a continuation of U.S. patent application Ser. No. 13/558,942, filed Jul. 26, 2012, now U.S. Pat. No. 8,931,159, which claims the benefit of the filing dates of U.S. Provisional Patent Application No. 61/666,187 filed Jun. 29, 2012 and U.S. Provisional Patent Application No. 61/512,637, filed Jul. 28, 2011, the disclosures of which are hereby incorporated herein by reference.

BACKGROUND OF THE INVENTION

The present disclosure relates to implantation of medical devices such as prosthetic heart valves and, more particularly, to assemblies and methods for loading a device such as a self-expanding collapsible heart valve into a delivery device.

Prosthetic heart valves may be formed from biological materials such as harvested bovine valves or pericardial tissue. Such valves are typically fitted within a stent, which may be inserted into the heart at the annulus of the compromised native valve to replace the native valve. To perform such insertion procedure using a minimally invasive technique, it is typically necessary to compress the stent to a reduced diameter for loading into the delivery device.

In the case of valves formed from biological materials, the stented valve is preferably preserved in the open condition for storage as compression of the valve material for extended periods compromises the integrity of the biological valve. It is therefore necessary to crimp the valve, or reduce its diameter for loading in the delivery device, in the operating arena.

Present crimping devices and methods for collapsing a stented valve, including direct radial assemblies, have proven to be unsatisfactory as they include bulky assemblies, are difficult to master, are time consuming, impart undue stress on the stented valve, or exhibit other undesirable qualities. Moreover, it is sometimes difficult to securely engage the stent to the retaining element of a delivery device. It would therefore be beneficial to provide a device and method for collapsing a stented bioprosthetic heart valve using apparatus and techniques that overcome the deficiencies of conventional devices. In addition, such devices and methods could be useful in the loading of the collapsed stented valve into a minimally invasive delivery device.

BRIEF SUMMARY OF THE INVENTION

One aspect of the invention provides an assembly for loading a self-expanding prosthetic device such as a prosthetic heart valve into a delivery device. An assembly according to this aspect of the invention desirably includes a compression member having a longitudinal axis, a first open end with a first diameter, a second open end with a second diameter less than the first diameter, and a wall decreasing in diameter in a distal direction from the first open end towards the second open end. This wall desirably defines an open space adapted to receive the prosthetic device.

The assembly according to this aspect of the invention desirably also includes a support member having a longitudinal axis, a base and a through bore extending along the longitudinal axis of the support member. The through bore preferably is sized to receive a portion of the delivery device therethrough. The support member may have a recess extending around the through bore, the recess being adapted to receive an end of the prosthetic device, the support member and the compression member being movable relative to one another between an initial position in which the base of the support member is relatively far from the first open end of the compression member and an operative position in which the base of the support member is relatively close to the first open end of the compression member. Thus, movement of the support member and the compression member from the initial position to the operative position can pushes the prosthetic device at least partially through the open space such that at least a portion of the prosthetic device is radially compressed by the tapered wall of the compression member as the prosthetic device advances through the open space.

The assembly according to this aspect of the invention desirably further includes a constricting member having a lumen defined therethrough, the lumen having proximal end and a distal end, the proximal end of the lumen desirably being sized to receive the second open end of the compression member. The distal end of the lumen desirably is sized to slidably receive at least a portion of the delivery device.

As discussed further below, in certain embodiments the constricting member can aid in movement of the prosthetic device into the sheath of the delivery device. Moreover, the constricting member can also act to seal the compression member to the distal sheath, so that the compression member and sheath may be filled with a liquid to displace air from the delivery device and prosthetic device.

In certain embodiments, the support member includes a longitudinally-extending slot which facilitates removal of the support member from the delivery device.

A further aspect of the invention provides methods for loading a self expanding prosthetic device into a delivery device. The delivery device used in the method typically includes a distal tip, a proximal conical end, a retaining element, a compartment defined between the proximal conical end and the retaining element and adapted to receive the prosthetic device. The device may also include a distal sheath movable between a closed position fully covering the compartment and an open position uncovering the compartment. The prosthetic device including a stent, and desirably also includes at least one retainer at one end of the stent, the prosthetic valve having an expanded condition and a collapsed condition. The method according to this aspect of the invention desirably includes inserting the prosthetic device in the expanded condition into a compression member having an inner surface which decreases in diameter progressively from a first open end to a second open end, and initially advancing the prosthetic device through the compression member until the at least one retainer protrudes from the second open end of the compression member. The method desirably further includes advancing a delivery device through the first open end of the compression member until the at least one retainer of the prosthetic device is disposed near the retaining element of the delivery device and moving the distal sheath of the delivery device into an open position to uncover the compartment, and attaching the at least one retainer of the prosthetic device to the retaining element of the delivery device. After such attachment, the distal sheath of the delivery device can be moved toward the closed position, and the prosthetic device can be further advanced through the second open end of the compression member.

Desirably, the method according to claim further includes filling at least a portion of the compression member with a sterile liquid to remove air from the prosthetic device and the delivery device before moving the distal sheath of the delivery device to the closed position.

BRIEF DESCRIPTION OF THE DRAWINGS

Various embodiments of the present loading assembly are disclosed herein with reference to the drawings, wherein:

FIG. 7 is a longitudinal cross-sectional view of a constricting member in accordance with an embodiment of the present invention;

FIG. 8 is an enlarged longitudinal cross-sectional view of an end section of the constricting member of FIG. 7;

DETAILED DESCRIPTION

Figure 1:
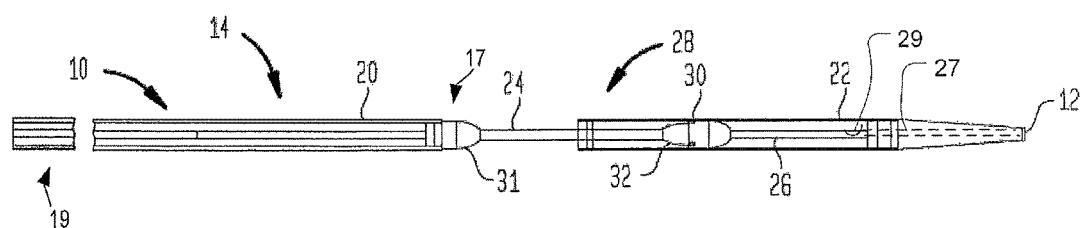
FIG. 1 is a perspective view of a distal portion of a delivery device.

Embodiments of the presently disclosed loading assemblies are described herein in detail with reference to the drawing figures, wherein like reference numerals identify similar or identical elements. In the drawings and in the description which follows, the term "proximal" refers to the end of a delivery device, or portion thereof, which is closest to the operator in use, while the term "distal" refers to the end of the delivery, or portion thereof, which is farthest from the operator in use when the delivery device is inserted into a patient. When used with reference to elements of a loading assembly or loading method, the term "proximal" refers to the direction toward the proximal end of the delivery device, whereas the term "distal" refers to the direction toward the distal end of the delivery device.

Figure 2:
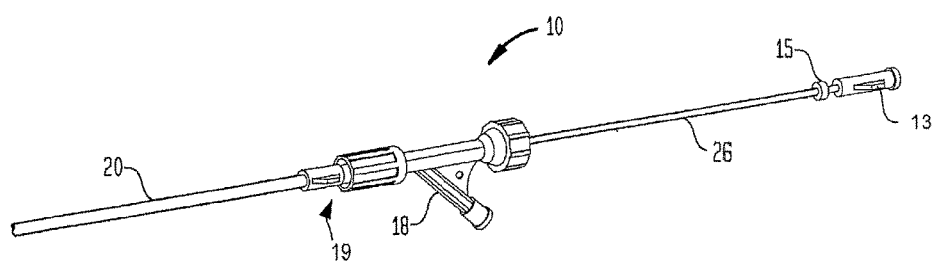
FIG. 2 is a perspective view of a proximal portion of the delivery device of FIG. 1.

As seen in FIGS. 1 and 2, a delivery device 10 used in one embodiment of the invention includes a catheter assembly 14 having a proximal end 19 and a distal end 17 (FIG. 1). The catheter assembly 14 has an outer shaft 20 extending between the proximal and distal ends. A proximal conical end 31 is fixed to the distal end 17 of catheter assembly 14. A hollow inner shaft 24 is fixed to the proximal conical end 31 and projects distally from the proximal conical end 31. A distal conical end 32 and retaining element 30 are mounted to inner shaft 24 remote from the proximal conical end 31, so that the distal conical end 32 and retaining element 30 are disposed distal to the proximal conical end 31. The conical ends thus define a valve receiving compartment 28 between them. For delivery into a patient, a collapsible valve is loaded into the valve receiving compartment 28 around the inner shaft 24 and between the conical ends 31 and 32, and the stent portion of the valve is coupled to the retaining element 30. When the valve is loaded in compartment 28 and distal sheath 26 is in the fully closed position, distal sheath encloses the valve.

A hollow inner tube 26 has a hub 13 (FIG. 2) at its proximal end, a distal tip 12 (FIG. 1) at its distal end, and a lumen extending from the hub to the distal tip. The lumen of inner tube communicates with a bore 27 in distal tip 12. In use, a guidewire can be threaded through the lumen to inner tube 26 and out through the bore 27 in distal tip 12 so that the guidewire extends distal to the distal tip 12. A distal sheath 22 is mounted to distal tip 12 and extends proximally from the distal tip. Distal sheath 22 has substantially the same diameter as outer shaft 20. The lumen of inner tube 26 communicates with the interior space within sheath 22 through a port 29 adjacent the distal end of the sheath. Inner tube 26 is slidably received within catheter assembly 14 and inner shaft 24. Thus, inner tube 26, distal tip 12 and distal sheath 22 can be moved proximally and distally relative to catheter assembly 14 and conical ends 31 and 32, between a fully closed position in which distal sheath 22 covers compartment 28 and the conical ends, and a fully open position in which the compartment is uncovered and the proximal end of distal sheath 22 is distal to retaining element 30.

Hub 13 is adapted for connection to another system or mechanism, such as an operating handle (not shown) for displacing tube 26 and the distal sheath 22 relative to catheter 14 and the retaining element 30. Mechanisms for displacing the distal sheath 22 between its proximal and distal positions are described in International Patent Application Publication No. WO/2009/091509, the disclosure of which is hereby incorporated by reference herein. A retaining ring 15 may be mounted on the inner tube 26 near hub 13.

A fitting such as a Y connector 18 may also be connected at the proximal end 19 of outer shaft 20, and may include a hemostasis valve for hindering blood flow out from between the inner tube 26 and the outer shaft 20. The Y connector 18 may also be coupled to a fluid source for flushing the outer shaft 20 and for injecting fluids such as contrast media during a prosthetic valve implantation procedure.

Figure 3:
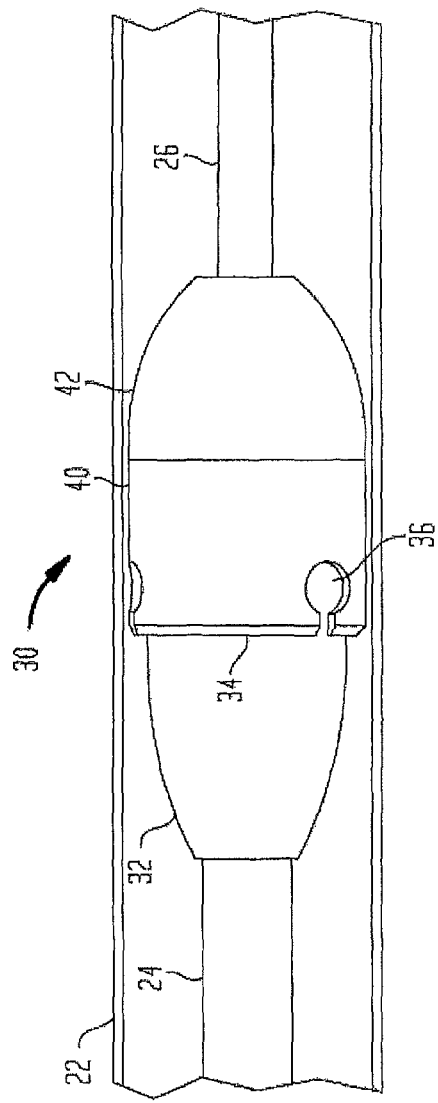
FIG. 3 is an enlarged side view of a retaining element of the delivery device shown in FIG. 1.

Referring now to FIG. 3, the retaining element 30 includes an outer piece 40, a support piece 42 located adjacent to the outer piece 40, and an inner piece (not shown, but attached to the outside of the inner shaft 24) that is coupled to the outer piece 40 so as to be rotatable relative thereto. The outer piece 40 defines one or more recesses 36, each recess 36 being located at a retention edge 34 of the outer piece 40 and configured to receive a corresponding retention member of the stent portion of a collapsible prosthetic valve. Each recess 36 preferably has a similar shape and a slightly larger size than a retention member 118 on a stent (FIG. 4) so as to capture same readily, but with only a small amount of relief therebetween. The recesses 36 are spaced apart from one another and each is sized and shaped to receive a tab or retainer 118 on one end of the prosthetic heart valve to maintain the prosthetic heart valve in assembled relationship with the delivery device 10, to minimize longitudinal movement of the prosthetic heart valve relative to the delivery device during unsheathing and resheathing procedures, to help prevent rotation of the prosthetic heart valve relative to the delivery device as the delivery device is advanced to the target site and during deployment and to maintain the alignment of the stent cells and prevent them from becoming tangled.

Figure 4:
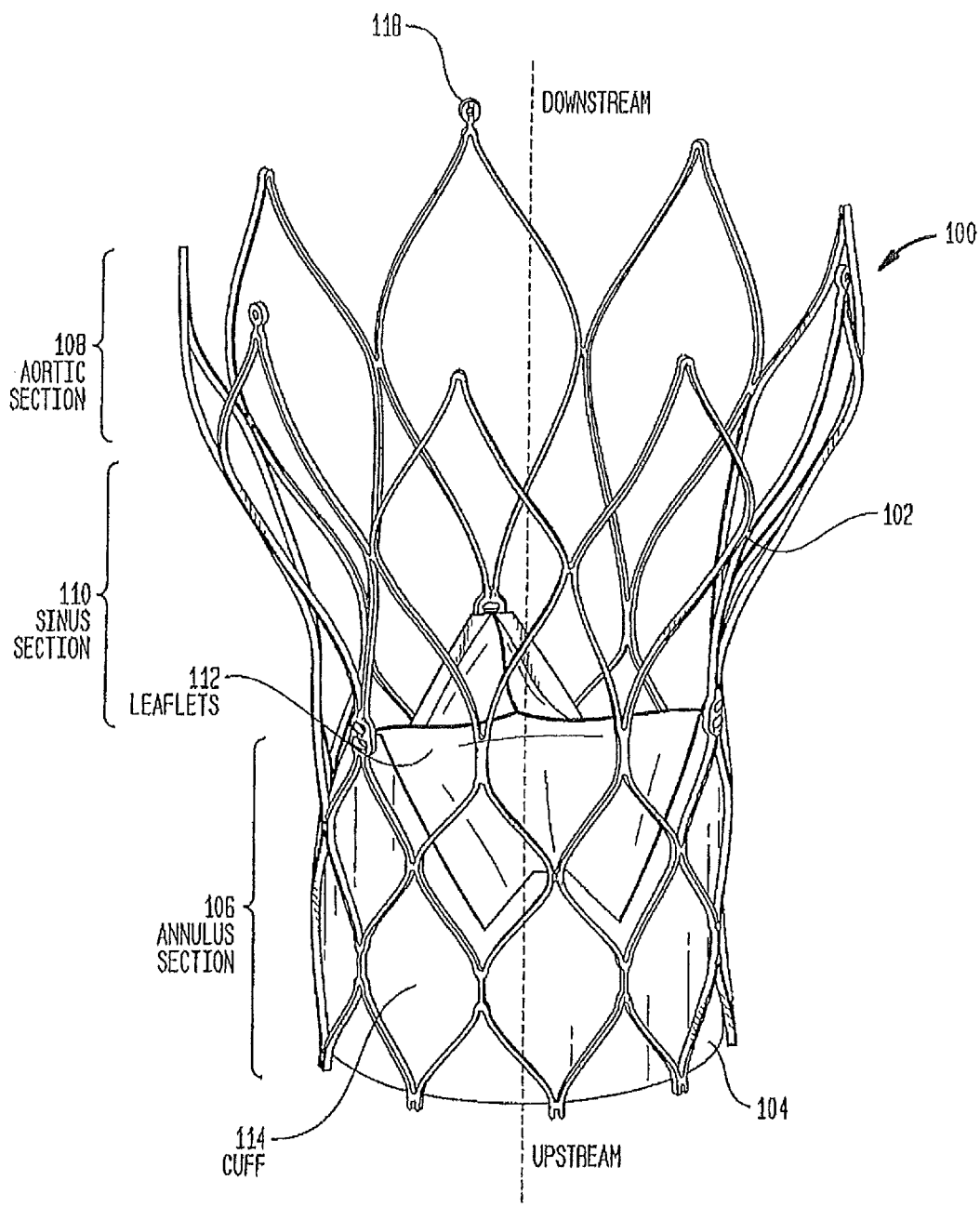
FIG. 4 is a perspective view of a self-expanding prosthetic heart valve.

FIG. 4 shows a bioprosthetic valve 100 such as that described in U.S. Patent Publication No. 2012/0053681, the contents of which are hereby incorporated by reference. Prosthetic valve 100 is designed to replace a native aortic valve. The valve 100 has a collapsed condition and an expanded condition and may be formed from a collapsible framework or stent 102, with a valve assembly 104 internally connected to the stent. The stent 102 may be formed from any suitable biocompatible material, such as nitinol or any other suitable elastic or shape memory material, and may include an annulus section 106, an aortic section 108, and a sinus section 110 located between the annulus section and the aortic section. The aortic section 108 may have a larger cross section than the annulus section 106. The valve assembly 104 includes a plurality of leaflets 112 and a cuff 114 attached to the stent 102. The leaflets 112 and the cuff 114 may be formed from a biocompatible polymer, from natural tissue such as bovine or porcine pericardial tissue, or from other appropriate biocompatible materials. The valve assembly 104 is preferably connected to the stent 102 generally within the annulus section 106. The valve 100 may include a plurality of tabs or retainers 118 at spaced positions around one or both ends of the stent 102 for engagement with the retaining element 30 of the delivery device 10 as described above. The retainers 118 may also be utilized to collapse the valve 100 for loading into the delivery device 10, as will be discussed below.

The valve 100 is preferably stored in its expanded or open condition as the bioprosthetic valve assembly 104 may be compromised by storage in a collapsed condition for extended periods of time. As such, it is necessary to crimp the valve 100 into a collapsed condition of reduced cross section for loading into the delivery device 10 at the latest possible time prior to the surgical implantation procedure. In order to effectively limit the time period the valve 100 is collapsed, the crimping process is preferably conducted in the operating arena by the surgeon, interventional cardiologist or surgical assistant using a specialized assembly.

Figure 5:
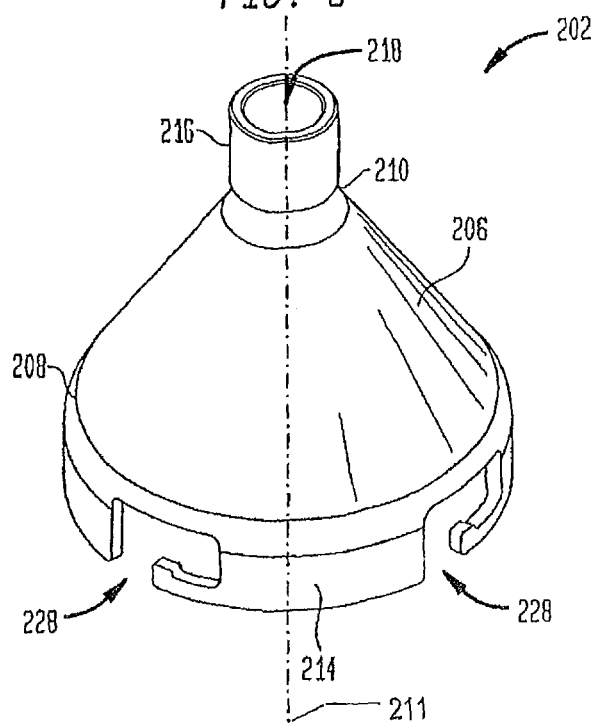
FIG. 5 is a perspective view of a compression member in accordance with an embodiment of the present invention.

FIGS. 5-6 illustrate a loading assembly 200 according to one embodiment of the present invention, the loading assembly generally including a compression member 202 and a support member 204 adapted to be coupled to one another. The compression member 202 includes a funnel 206 having a longitudinal axis 211 and a substantially frustoconical shape with a large diameter at a first open end 208 and a smaller diameter at a second open end 210. The interior diameter of the funnel 206 decreases progressively from the first end 208 to the second end 210. The compression member 202 is preferably made of a substantially rigid material, and may be wholly or partly made of a transparent plastic, such as polycarbonate or acrylic, to allow viewing of the valve 100 during loading.

The compression member 202 may further include an annular rim 214 extending from the first end 208 of the funnel 206 for joining the compression member to the support member 204 as described below. The rim 214 may include a plurality of slots 228 disposed around its outer periphery. While the drawings show slots 228 that are substantially P-shaped, the slots may have any other shapes suitable for securely holding the compression member 202 to the support member 204. The rim 214 may include four such slots 228, or more or less than four. Regardless of the number or slots 228, the slots are preferably spaced equidistantly from each other.

The compression member 202 also may include a tubular extension 216 projecting from the second end 210 of the funnel 206. The tubular extension 216 has an opening 218 therethrough in communication with the interior of funnel 206. The opening 218 is sized and shaped to receive the distal sheath 22 of the delivery device 10 therein. The cross section of the tubular extension 216 is preferably substantially circular, but may be oblong, oval, elliptical, or polygonal.

With reference to FIGS. 6A, 6B, 6C and 9, the support member 204 is preferably made in whole or in part of a substantially rigid material, and includes a body 219 having a substantially flat or planar bottom support surface 220 and a top end 221. Body 219 has an outer wall 232, a longitudinal axis 231 and a generally cylindrical bore 230 extending longitudinally through the support member. Bore 230 is sized and shaped to receive at least a portion of the tip 12 of the delivery device 10 therein. A recess 226 extends downwardly from the top end 221 of the body 219 concentrically with bore 230 so as to define an annular ridge 244 at a spaced distance from the top end. Ridge 244 may have a chamfered surface 246 at its intersection with bore 230. Alternatively, a chamfered surface 246 may not be included. Recess 226 has a diameter and a depth defined by ridge 244 sufficient to receive at least a portion of the annulus section 106 of the stent 102 in an expanded condition.

Figure 6A:
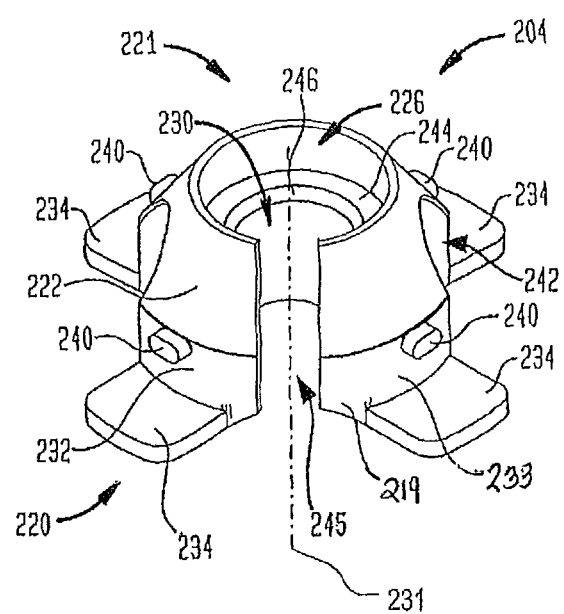
FIG. 6A is a perspective view of a support member in accordance with an embodiment of the present invention.

The outer wall 232 of body 219 does not extend continuously around the body, but rather is interrupted by a plurality of inwardly curved indentations 242 which divide the outer wall into a plurality of wall segments 233, only two of which are shown in FIG. 6A. Although FIG. 6A depicts a support member 204 having three indentations 242 evenly spaced around the periphery of body 219, it is contemplated that the support member may be provided with more or less than three such indentations. Indentations 242 facilitate the grasping of support member 204. Between indentations 242, that is, in the space between outer wall segments 233 and bore 230, body 219 may include a plurality of recesses 235 extending inwardly from the bottom support surface 220. Recesses 235 reduce the mass of body 219 and facilitate the manufacturing process by eliminating excessively thick portions of the body.

The outer wall segments 233 of body 219 do not extend all the way to the top end 221 of the body, but rather terminate at their top ends at a tapered wall 222 oriented at an oblique angle to the outer wall 232. At their bottom ends, outer wall segments 233 each include a radially projecting supporting plate 234, the bottom surfaces of which are substantially coplanar with the bottom support surface 220 of body 219. At least one pin 240 may protrude radially outward from each outer wall segment 233. Pins 240 are preferably spaced a sufficient distance from supporting plates 234 and sized and shaped to be received in the slots 228 of the compression member 202 to join the compression member and the supporting member 204 together.

Figure 6B:
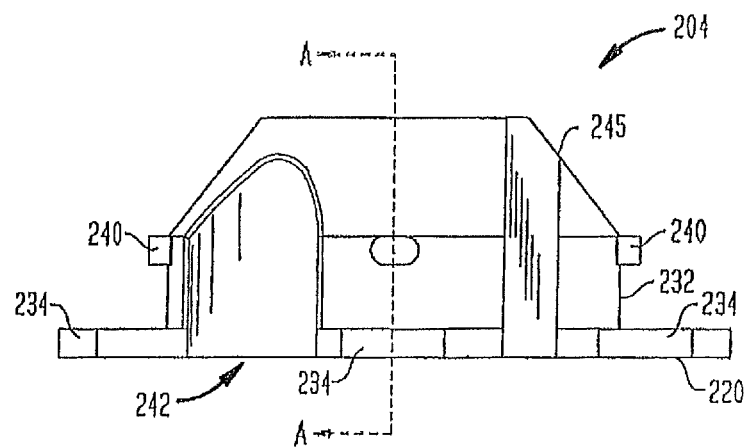
FIG. 6B is a side elevational view of the support member of FIG. 6A.
Figure 6C:
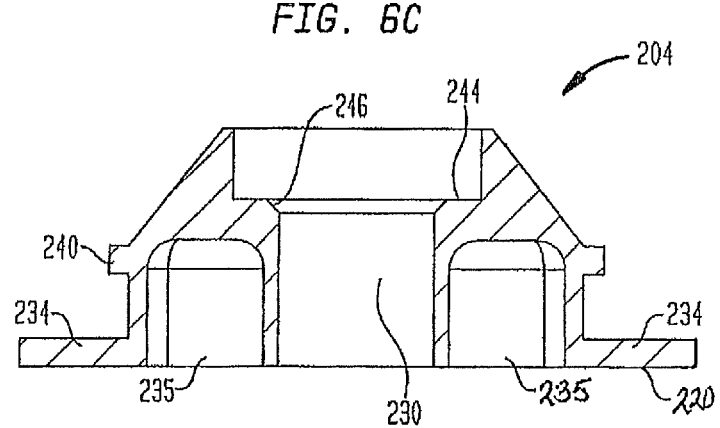
FIG. 6C is a cross-sectional view of the support member of FIG. 6A, taken along section line A-A of FIG. 6B.

As illustrated, body 219 is also be interrupted by slit 245 as seen in FIGS. 6A and 6B. Slit 245 may formed as a longitudinal cutout in outer wall 232 and tapered wall 222, extending along the length of body 219 and in communication with bore 230 to allow removal of support member 204 after a heart valve has been loaded into delivery device 10.

Slit 245 may be sized so as to allow outer shaft 20 or distal sheath 22 disposed within bore 230 to be removed through the slit.

FIGS. 7 and 8 illustrate a constricting member 300 designed to aid in loading of a prosthetic heart valve into delivery device 10. The constricting member 300 may be wholly or partly made of a transparent plastic, such as polycarbonate or acrylic, to allow viewing of the delivery device 10 during loading. Constricting member 300 includes a tubular body 302 having a central lumen 304 sized and shaped to slidingly receive the outer shaft 20 and distal sheath 22 of the delivery device 10. Lumen 304 includes a counterbore 316 at the proximal end of the lumen having a diameter sized and shaped to receive the tubular extension 216 of the compression member 202. Preferably, the diameter of counterbore 316 is only slightly larger than the outer diameter of the tubular extension 216 so as to create a friction fit therebetween. Lumen 304 further includes a tapered portion 310. In particular, tapered portion 310 may have an inner surface 312 which tapers from a larger diameter at its end adjacent the counterbore 316 to a smaller diameter at its other end to help compress valve 100 further during loading into delivery device 10.

Turning back to FIG. 7, lumen 304 further includes a secondary taper 320 adjacent the distal end of the lumen and a distal end section 321 extending from the secondary taper to the distal end of the lumen. The small end of the secondary taper 320 and distal end section 320 may sized and shaped to receive at least the distal sheath 22 of the delivery device 10. An annular groove or other indicator line 324 may extend partly or entirely around the outer periphery of the tubular body 302. Line 324 helps correctly position the delivery device within the loading system. Constricting member 300 may further include a proximal seal 325 and a distal seal 327 disposed within lumen 304 near the two ends of the constricting member. In some examples, each seal 325 and 327 includes an O ring. The constricting member also includes an enlarged head 308 at its proximal end. As discussed in detail below, using the constricting member 300 helps to load the valve 100 into the delivery device 10 and reduces the loading forces (i.e., the forces required to load the valve into the delivery device).

Figure 9:
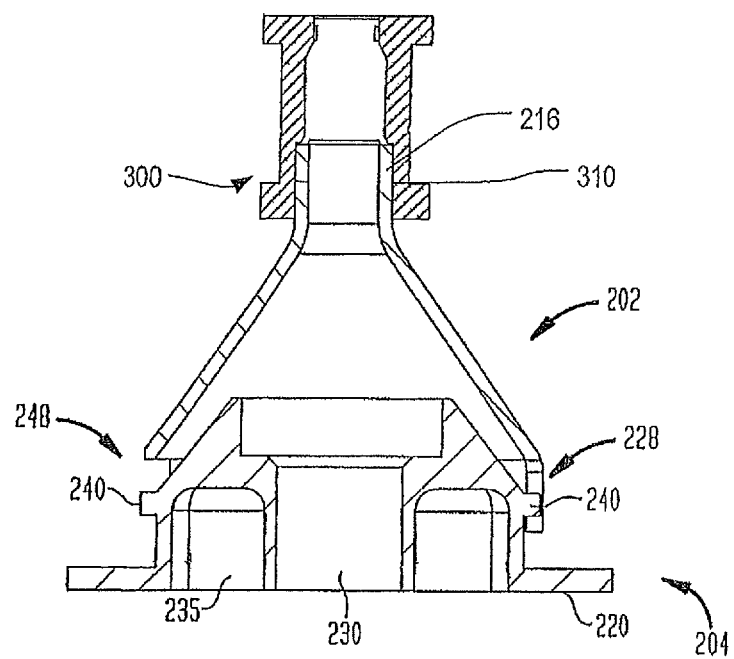
FIG. 9 is a longitudinal cross-sectional view of a loading assembly in accordance with an embodiment of the present invention, including the compression member of FIG. 5, the support member of FIG. 6A, and the constricting member of FIG. 7.

FIG. 9 shows an assembled loading assembly 200 including the compression member 202 of FIG. 5, the support member 204 of FIG. 6 and the constricting member 300 of FIG. 7. As seen in FIG. 9, the constricting member 300 is connected to the tubular extension 216 of the compression member 202, the tubular extension being received within the counterbore 316 of the constricting member. In the depicted condition, the compression member 202 is locked to the support member 204. To lock the compression member 202 to the support member 204, the pins 240 of the support member are inserted into the slots 228 of the compression member (FIG. 5), and the compression member is turned relative to the support member to slide the pins toward the closed ends of the slots. Hence, the pins 240 and the slots 228 together form a locking mechanism 248.

Figure 10:
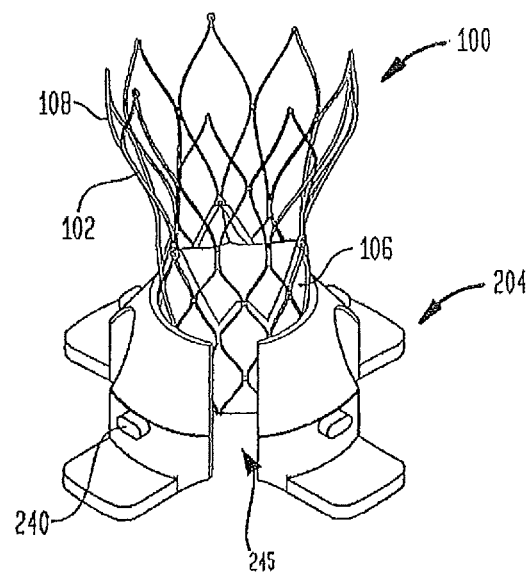
FIGS. 10-19 illustrate the steps of a method for loading a prosthetic heart valve into a delivery device using the loading assembly of FIG. 9.
Figure 11:
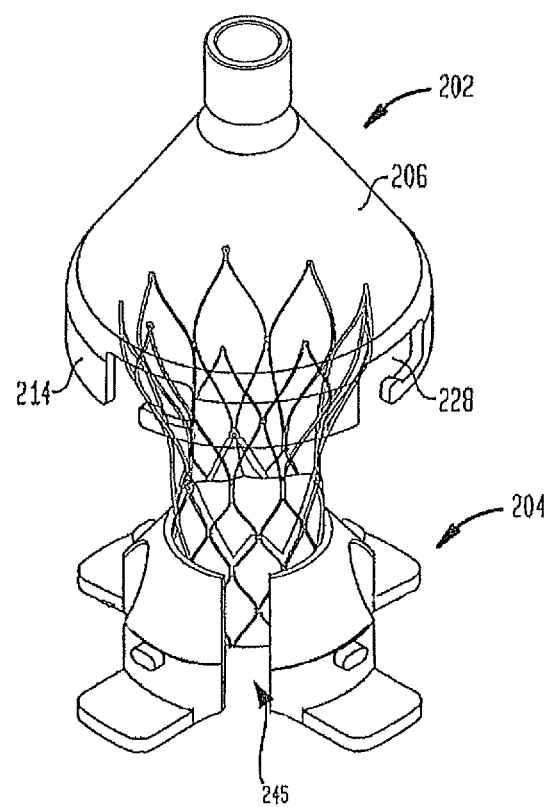
Figure 12:
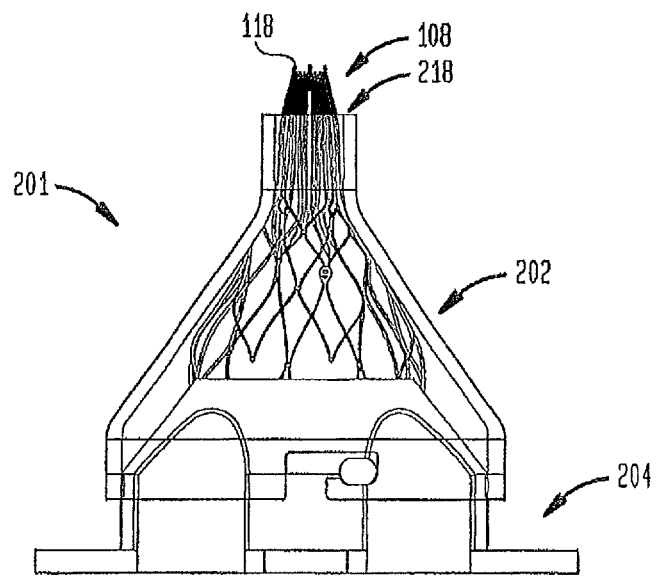
Figure 13:
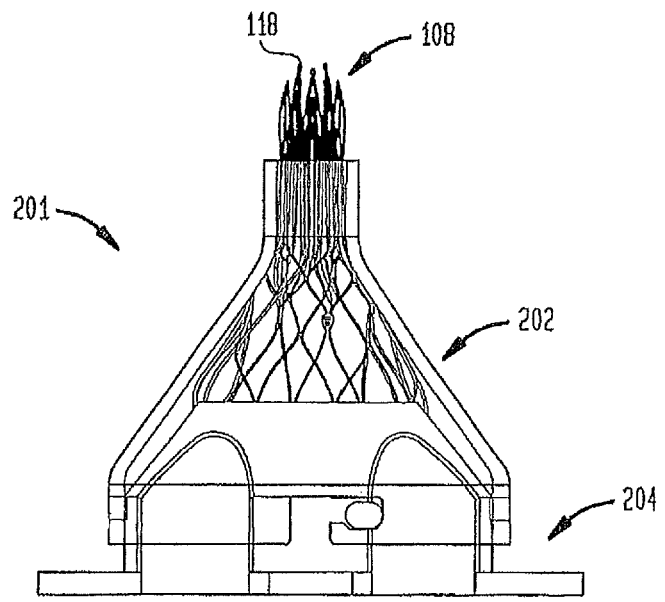

In an exemplary method of use, as seen in FIGS. 10-19, the loading assembly 200 is used to load the collapsible prosthetic heart valve 100 into a delivery device 10. As shown in FIG. 10, with the supporting member 204 on a flat surface, at least a portion of the annulus section 106 of the stent 102 may be placed within the recess 226 of the support member until the end of the stent contacts ridge 244. The compression member 202 may then be placed over the aortic section 108 of the stent 102 so that the aortic section of the stent is positioned within the funnel 206, as depicted in FIG. 11. As shown in FIG. 13, the compression member 202 and the support member 204 may then be pushed together, the tapered walls of the funnel 206 gradually compressing the valve 100 until a portion of the aortic section 108 of the stent 102 is forced into and through the opening 218 of the compression member. When a portion of the aortic section 108 of the stent 102 passes through the opening 218 of the compression member 202, the retainers 118 of the stent will protrude through the opening 218 and will be positioned closely adjacent to one another. At this point, the pins 240 of the support member 204 will be positioned within the slots 228 of the compression member 202, and the members may be locked together by rotating the support member relative to the compression member, such that the pins 240 of the support member slide toward the closed ends of the slots 228 of the compression member.

Figure 14A:
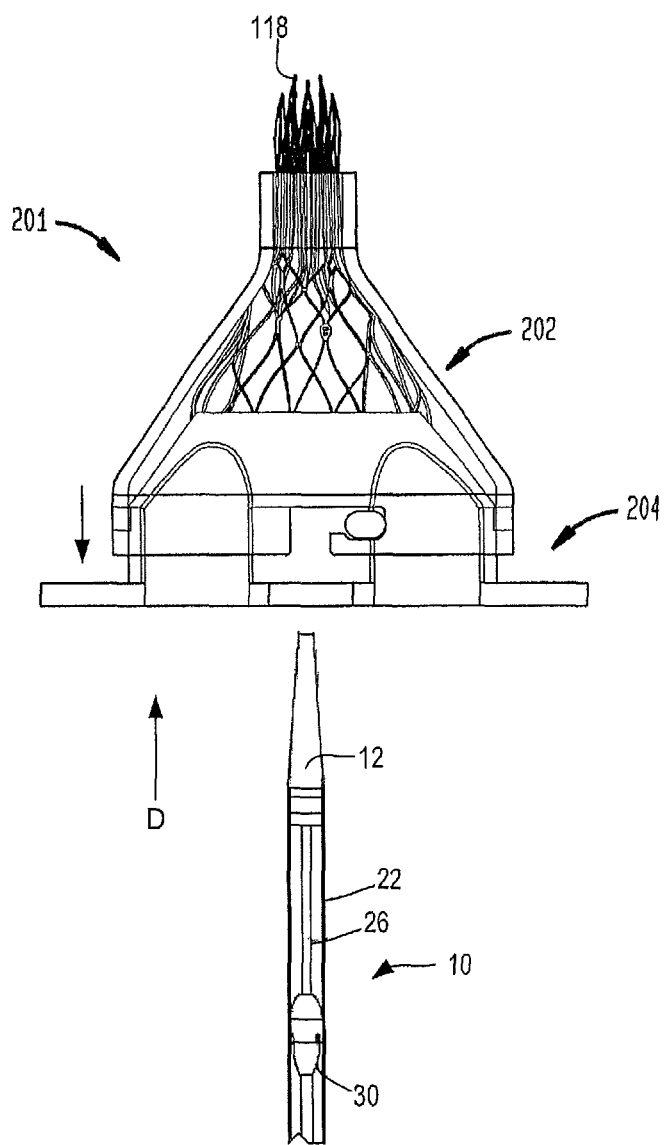

As seen in FIG. 14A, the distal tip 12 and the distal sheath 22 of the delivery device 10 may be inserted from the bottom of bore 230 of support member 204. To accomplish this, the compression member 202 and the support member 204 may be squeezed closer together as seen in FIGS. 12-13. The dimension of the slots 228 in the longitudinal direction, i.e., the height of the slots, is greater than the dimension of the pins 240 in the longitudinal direction, i.e., the height of the pins. Therefore, even though the compression member 202 and the support member 204 are assembled together, they still may move further toward one another. As the compression member 202 and the support member 204 move closer together, a greater portion of the stent 102 is forced out through opening 218, causing the retainers 118 to begin to separate from one another, as illustrated in FIG. 14A. The distal tip 12 and distal sheath 22 of the delivery device 10 may then be advanced through support member 204, compression member 202 and valve 100, as indicated by arrow D.

Figure 14B:
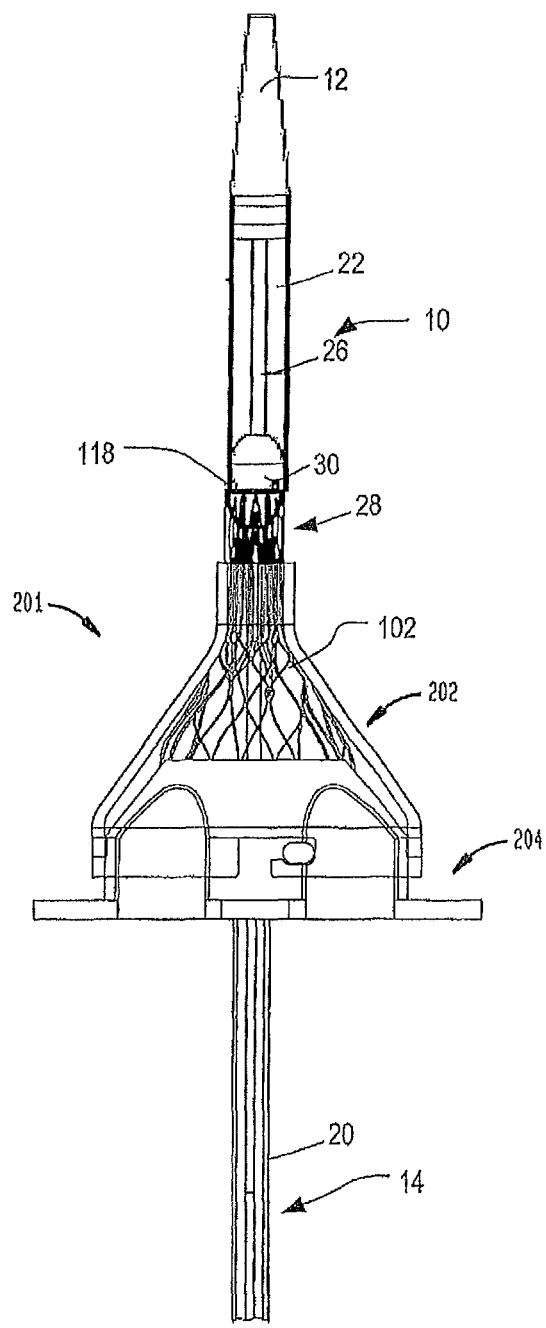

As seen in FIG. 14B, the delivery device 10 is advanced through loading assembly 201 and the distal tip 12 and distal sheath 22 slid distally with respect to catheter 14 to expose retaining element 30. Delivery device 10 may then be aligned with the loading assembly such that retainers 118 of prosthetic valve 100 are positioned within valve receiving compartment 28 near retaining element 30 of the delivery device 10. The loading assembly 201 may be twisted as needed to align the retainers 118 with the recesses 36 in the retaining element 30. The resilience of the stent tends to urge retainers 118 radially inward, into recesses 36 (FIG. 3) of the retaining element 30. Once the retainers drop into the recesses, the operator can retract the distal tip and distal sheath slightly relative to the catheter 14 until the proximal edge of sheath 22 overlies the retaining element. In this condition, the retainers on the stent are captured securely within the recesses of the retaining element, so that the stent 102 is securely attached to the retaining element and to the delivery device 10.

Figure 15:
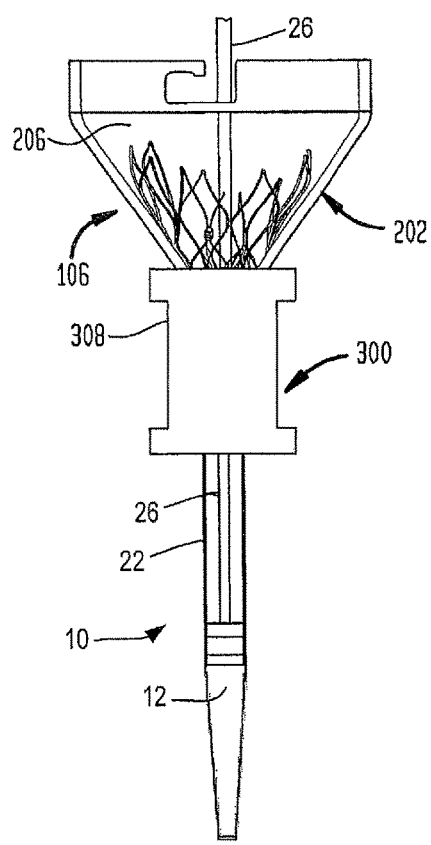

With the stent 102 attached to retaining element 30, support member 204 may be removed by decoupling pins 240 from slots 228. Support member 204 may then be removed from the assembly by sliding proximally along catheter 14 and passing proximal sheath 20 through slit 245 (FIG. 6A). FIG. 15 shows valve 100 loaded into compression member 202 after support member 204 has been removed. Constricting member 300 may be slid onto distal sheath 22 and over tubular extension 216 of compression member 202. In this condition, the proximal seal 325 (FIG. 8) of the constricting member engages the tubular extension on the compression member, whereas distal seal 327 (FIG. 8) of the constricting member engages the outside of the distal sheath 22. The constricting member and seals thus seal the compression member to the distal sheath 22 of the delivery device.

Figure 16:
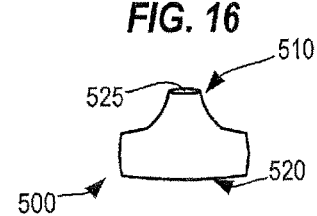
Figure 17:
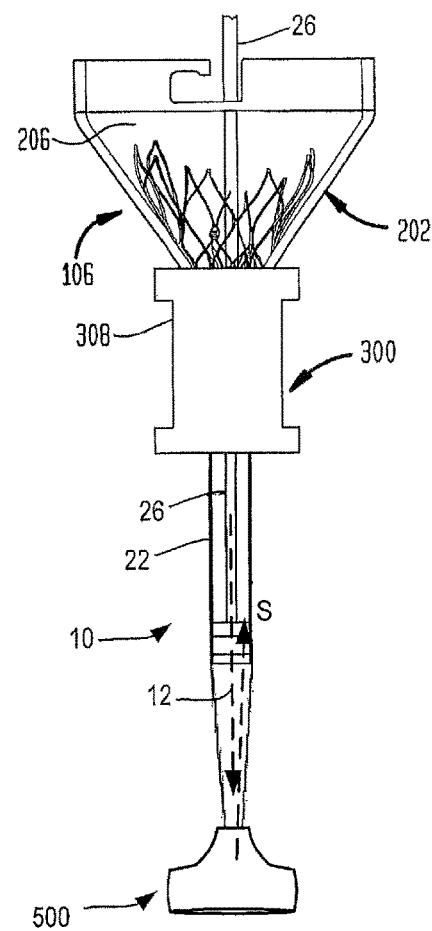

FIG. 16 illustrates a distal plug 500 for use with transapical delivery device 10. Distal plug 500 includes a first end 510 and a second end 520. Distal plug 500 increases in diameter between first end 510 and second end 520 and includes an aperture 525 for accepting distal tip 12 of delivery device 10 and plugging the distal tip. FIG. 17 illustrates distal plug 500 disposed on distal tip 12, effectively sealing the opening of passageway 27 (FIG. 1) in the distal tip.

Figure 18:
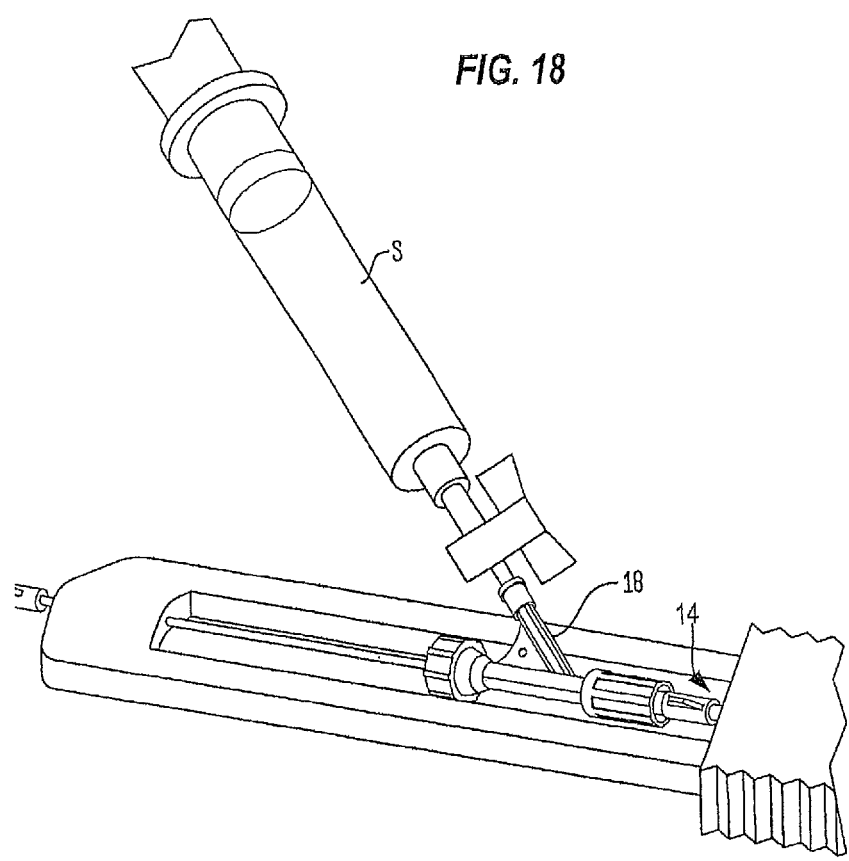

As seen in FIG. 18, with distal plug 500 sealing distal tip 12, a deairing process may be initiated. A syringe S may be connected to the Y connector 18 of the proximal portion of the delivery device of the delivery device 10, as shown in FIG. 18. The syringe may be used to inject a sterile liquid, such as saline, into the proximal end of catheter 14 and out toward valve 100, thereby flushing the air from the device. During this flushing step, the distal end of the delivery device may be tapped multiple times to facilitate the air removal.

Additional portions of the sterile liquid are introduced through fitting 13 (FIG. 2) at the proximal end of hollow inner tube 26, while the delivery device is oriented as shown in FIG. 17, with the distal tip pointing downwardly. Because distal plug 500 seals the distal tip 12, sterile liquid introduced through hollow tube 26 passes out of the hollow tube through the port 29 (FIG. 1) and fills the distal sheath from the distal end. The liquid returns back up toward prosthetic valve 100 as seen by arrow S and into the compression member 202. This action helps to remove air from the valve.

Figure 19:
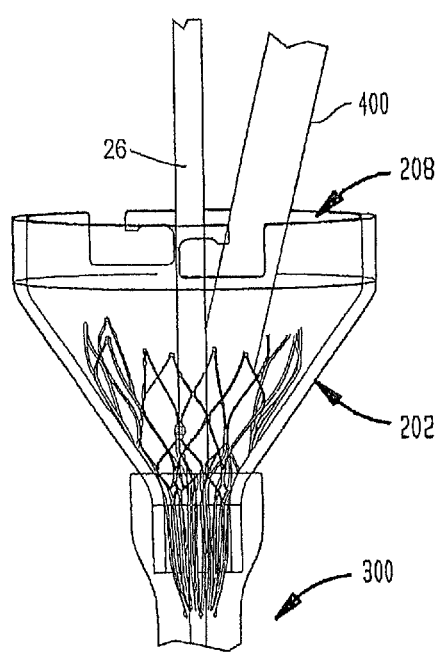

As seen in FIG. 19, additional sterile liquid, such as saline, may be dispensed into the compression member 202. With the first open end 208 of the funnel 206 facing up, the sterile liquid may be dispensed into the compression member 202 through the first open end. The sterile liquid may be dispensed into the compression member 202, such as through a syringe or a sterile container, until the funnel 206 is substantially filled. The syringe may need to be refilled several times during the injection process in order to fill the funnel 206 with the sterile liquid.

Any air bubbles in the sterile liquid within the funnel 206 may then be removed. It is important that little or no air be released into the human body during deployment and/or resheathing of the valve within the human heart, as the air may block vascular flow and cause tissue damage. For this reason, it is important to remove air bubbles from the delivery device 10 and the valve 100 before introducing them into the body. Testing has shown that, if the methods and assemblies described in this application are employed, minimal air will be released into the patient's bloodstream during valve deployment and resheathing.

Air bubbles formed in the sterile liquid near the space between the leaflets 112 and the cuff 114 of the valve 100 may be removed by using a tube or rod 400 or any other suitable atraumatic probe. The tube 400 is commonly known in the art as a "leaflet tester" and may be formed of a substantially soft material, such as a soft polymer. In order to remove the air bubbles from the sterile liquid, the tube 400 may be placed into the sterile liquid contained in the funnel 206 of the compression member 202 and used to probe areas of potential air entrapment, including gently agitating the liquid, as shown in FIG. 19. A syringe may be used to remove the air bubbles from the space near the retaining element 30 of the delivery device 10. To do so, the syringe may be inserted into the space near the retaining element 30, and the sterile liquid near the retaining element 30 may be gently agitated with the syringe.

After the air bubbles have been removed, distal sheath 22 of delivery device 10 may be retracted relative to catheter 14 until the valve is completely covered and disposed within valve receiving compartment 28. During this process, the compression member 202 moves proximally relative to catheter 14 along with the distal sheath, whereas the valve is held in place relative to the catheter by the retainers engaged in the retaining element 30. (FIGS. 1 and 14B.) Thus, the valve is advanced through the second end of the compression member and through the constricting member. The internal tapers in the lumen of the constricting member (FIGS. 7 and 8) aid in constricting the valve to fit within the distal sheath. This process continues until the valve is entirely disposed within the distal sheath 22 and the distal sheath comes to rest in the fully closed position, with the sheath lodged against the distal end of catheter 14. The compression member 202 may then be removed from the delivery device 10 by sliding it distally over distal sheath 22.

In an alternate method of loading the valve 100 into the delivery device 10 and preparing same for use in a patient, the air bubbles may be removed from the distal sheath 30 by submerging the distal sheath, the compression member 202, and the constricting member 300 in a container holding sterile liquid, such as saline. Additional sterile liquid may be injected into the delivery device 10 through the Y-connector 18 using a syringe, as discussed above. The distal sheath 30 of the delivery device 10 may then be shaken and gently tapped against a hard surface to remove air bubbles from the valve 100. The valve 100 may then pulled into the distal sheath 22, as discussed above.

In view of the tight fit between the collapsed valve 100 and distal sheath 22, significant friction forces must be overcome in order to move the distal sheath 22 completely over the valve 100. To facilitate this procedure, the stent 102 may be substantially cooled, which, depending on the materials forming the stent, may enable the stent to more easily deform. Thus, once more than about one-half of the length of the stent 102 has been covered by distal sheath 22, a cold liquid, such as saline solution, may be applied to the stent through the compression member 202 and the constricting member 300. This may be accomplished by removing the support member 204 from the compression member 202 and holding the remainder of the assembly in a substantially vertical orientation with the first end 208 of the funnel 206 facing upwardly. The cold liquid may then be introduced into the compression member 202 using any suitable apparatus. It will, of course, be appreciated that the cold liquid may thus serve two purposes-it may cool the stent 102, and it may serve as the deairing liquid in the deairing procedure described above.

In order for the cooling of the stent 102 to be effective in making it easier for the stent to be completely covered by the distal sheath 22 of the delivery device 10, the stent should be cooled to a temperature below the transition temperature of the material forming the stent. The "transition temperature" of a material is the temperature at which the material changes from one crystal state to another. For the nitinol stents that may be employed in the present invention, a saline solution at about 0° C. may be used. When cooled below its transition temperature, the stent 102 becomes plastic, enabling it to deform much more readily under the forces exerted by the movement of the distal sheath 22 thereover. Accordingly, after the stent 102 has been cooled below the transition temperature, the user may completely cover the stent 102 with the distal sheath 22 of the delivery device 10.

Although the invention herein has been described with reference to particular embodiments, it is to be understood that these embodiments are merely illustrative of the principles and applications of the present invention. The loading assembly, for example, may be modified in various ways. For example, a locking assembly to couple compression member 202 to support member 204 may include a male connecting member on one of the support member or the compression member, and a female connecting member on the other of the support member or the compression member for mating with the male connecting member. In addition to the pins discussed above, the female connecting member may include an annular groove extending along an inner surface of the first open end of the compression member, and the male connecting member may include a plurality of locking tabs on the support member adapted to engage the annular groove of the compression member so as to connect the support member to the compression member. Alternatively, the male connecting member may include an annular rim extending from the first open end of the compression member, and the female connecting member may include an annular slot on the support member sized to receive the rim so as to connect the compression member to the support member. Further alternatives such as partial screw threads, or clips can be used to lock these elements together.

In the embodiments discussed above, the loading apparatus is used to place a prosthetic heart valve into the delivery device. However, in other embodiments the loading apparatus and methods can be used to place other prosthetic valves incorporating self-expanding stents into a delivery device. Moreover, the loading apparatus and methods can be used to place stents which are not associated with valves into a delivery device. As used in this disclosure, the term "self-expanding prosthetic device" should be understood as embracing a device which includes a self-expanding stent, with or without a valve.

It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A method for loading a self-expanding prosthetic device into a delivery device, the delivery device including a distal tip, a proximal end, a retaining element, a compartment defined between the proximal end and the retaining element and adapted to receive the prosthetic device, and a distal sheath movable between a closed position fully covering the compartment and an open position uncovering the compartment, and the prosthetic device including a stent, and at least one retainer at one end of the stent, the prosthetic device having an expanded condition and a collapsed condition, the method comprising:
   placing the prosthetic device in the expanded condition between a support member and a compression member, the compression member having an inner surface which is variable in diameter between a first open end and a second open end;
   engaging the support member and the compression member to advance a portion of the prosthetic device through the compression member;
   moving the distal sheath of the delivery device into the open position to uncover the compartment;
   advancing the delivery device through the first open end of the compression member until the at least one retainer of the prosthetic device is disposed near the retaining element of the delivery device;
   attaching the at least one retainer of the prosthetic device to the retaining element of the delivery device;
   moving the distal sheath of the delivery device to the closed position; and
   removing the delivery device from the compression member.

2. The method according to claim 1, further comprising filling at least a portion of the compression member with a sterile liquid to remove air from the prosthetic device and the delivery device before moving the distal sheath of the delivery device to the closed position.

3. The method according to claim 2, further comprising agitating the sterile liquid in the compression member to facilitate removal of air from the prosthetic device and the delivery device.

4. The method according to claim 3, wherein the agitating step includes moving a syringe in the sterile liquid adjacent the retaining element of the delivery device.

5. The method according to claim 2, further comprising sealing the sheath of the delivery device to the compression member prior to the filling step.

6. The method according to claim 5, wherein the delivery device further includes a tube extending to the distal tip and communicating with a space within the sheath adjacent a distal end of the sheath, the method further comprising introducing sterile liquid into the sheath through the tube.

7. The method according to claim 6, wherein the tube communicates with a passage through the distal tip of the delivery device, coupling a distal plug to the distal tip of the delivery device to seal the passage prior to introducing sterile liquid through the tube.

8. The method according to claim 5, wherein the sealing step includes assembling a proximal end of a constricting member to the second open end of the compression member and sealing a distal end of the constricting member to the sheath of the delivery device, the step of further advancing the prosthetic device through the second open end of the compression member including advancing the prosthetic device through a lumen in the constricting member.

* * * * *